United States Patent [19]

Chang et al.

[11] Patent Number: 5,723,125
[45] Date of Patent: Mar. 3, 1998

[54] HYBRID WITH INTERFERON-ALPHA AND AN IMMUNOGLOBULIN FC LINKED THROUGH A NON-IMMUNOGENIC PEPTIDE

[75] Inventors: Tse Wen Chang; Liming Yu, both of Houston, Tex.

[73] Assignee: Tanox Biosystems, Inc., Houston, Tex.

[21] Appl. No.: 719,331

[22] Filed: Sep. 25, 1996

Related U.S. Application Data

[63] Continuation-in-part of Ser. No. 579,211, Dec. 28, 1995, abandoned.
[51] Int. Cl.$^6$ .................... A61K 39/395; A61K 39/00; C07K 16/00; C07K 1/00
[52] U.S. Cl. .................... 424/134.1; 424/185.1; 424/192.1; 435/69.7; 530/387.3; 530/351; 536/23.4
[58] Field of Search .................. 530/387.3, 351; 424/85.4, 134.1

[56] References Cited

U.S. PATENT DOCUMENTS 5,349,053  9/1994  Landolfi .................... 530/351

FOREIGN PATENT DOCUMENTS 0467416  1/1992  European Pat. Off.

OTHER PUBLICATIONS

Huston, JS et al Methods in Enzymology vol. 203 pp. 46–88, 1991.

Primary Examiner—Lila Feisee
Assistant Examiner—John Lucas
Attorney, Agent, or Firm—Eric P. Mirabel

[57] ABSTRACT

Disclosed is a hybrid recombinant protein consisting of human interferon, preferably interferon-α (IFNα), and human immunoglobulin Fc fragment, preferably γ4 chain, joined by a peptide linker comprising the sequence Gly Gly Ser Gly Gly Ser Gly Gly Gly Gly Ser Gly Gly Gly Gly Ser (SEQ ID NO:1).

4 Claims, No Drawings

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 48 nucleic acids
( B ) TYPE: nucleotide
( C ) STRANDEDNESS: double stranded
( D ) TOPOLOGY: linear ( x i ) SEQUENCE DESCRIPTION: SEQ ID NO:1:

```
GGT  GGC  TCA  GGT  GGA  TCC  GGT  GGA  GGC  GGA  AGC  GGC    36
Gly  Gly  Ser  Gly  Gly  Ser  Gly  Gly  Gly  Gly  Ser  Gly
 1                  5                        10

GGT  GGA  GGA  TCA    48
Gly  Gly  Gly  Ser
             1 5
```

( 2 ) INFORMATION FOR SEQ ID NO:2:

( i ) SEQUENCE CHARACTERISTICS:
( A ) LENGTH: 6 amino acids
( B ) TYPE: amino acid
( D ) TOPOLOGY: unknown ( x i ) SEQUENCE DESCRIPTION: SEQ ID NO:2:

```
Gly  Gly  Ser  Gly  Gly  Ser
 1                  5
```

( 2 ) INFORMATION FOR SEQ ID NO:3:

(i) SEQUENCE CHARACTERISTICS:
    (A) LENGTH: 81 nucleic acids
    (B) TYPE: nucleic acid
    (C) STRANDEDNESS: single stranded
    (D) TOPOLOGY: linear (xi) SEQUENCE DESCRIPTION: SEQ ID NO:3:

```
CATAAGCTTC ATCTACAATG GCCTTGACCT TTGCTTTACT        40
GGTGGCCCTC CTGGTGCTCA GCTGCAAGTC AAGCTGCTCT G      81
```

(2) INFORMATION FOR SEQ ID NO:4:

(i) SEQUENCE CHARACTERISTICS:
        (A) LENGTH: 40 nucleic acids
        (B) TYPE: nucleic acid
        (C) STRANDEDNESS: single stranded
        (D) TOPOLOGY: linear (xi) SEQUENCE DESCRIPTION: SEQ ID NO:4:

```
CTCTGCGGAT CCACCTGAGC CACCTTCCTT ACTTCTTAAA        40
```

(2) INFORMATION FOR SEQ ID NO:5:

(i) SEQUENCE CHARACTERISTICS:
        (A) LENGTH: 58 nucleic acids
        (B) TYPE: nucleic acid
        (C) STRANDEDNESS: single stranded
        (D) TOPOLOGY: linear (xi) SEQUENCE DESCRIPTION: SEQ ID NO:5:

```
AATGGATCCG GTGGAGGCGG AAGCGGCGGT GGAGGATCAG        40
AGTCCAAATA TGGTCCCC                                58
```

(2) INFORMATION FOR SEQ ID NO:6:

(i) SEQUENCE CHARACTERISTICS:
        (A) LENGTH: 42 nucleic acids
        (B) TYPE: nucleic acid
        (C) STRANDEDNESS: double stranded
        (D) TOPOLOGY: linear (xi) SEQUENCE DESCRIPTION: SEQ ID NO:6:

```
ATCGAATTCT ATTTACCCAG AGACAGGGAG AGGCTCTTCT GT     42
```

(2) INFORMATION FOR SEQ ID NO:7:

(i) SEQUENCE CHARACTERISTICS:
        (A) LENGTH: 1302 nucleic acids
        (B) TYPE: nucleic acid
        (C) STRANDEDNESS: double stranded
        (D) TOPOLOGY: linear (xi) SEQUENCE DESCRIPTION: SEQ ID NO:7:

```
ATG  GCC  TTG  ACC  TTT  GCT  TTA  CTG  GTG  GCC  CTC  CTG  GTG        39
Met  Ala  Leu  Thr  Phe  Ala  Leu  Leu  Val  Ala  Leu  Leu  Val
 1              5                        10

CTC  AGC  TGC  AAG  TCA  AGC  TGC  TCT  CTG  GGC  TGT  GAT  CTG        78
Leu  Ser  Cys  Lys  Ser  Ser  Cys  Ser  Leu  Gly  Cys  Asp  Leu
         15                  20                       25

CCT  CAA  ACC  CAC  AGC  CTG  GGT  AGC  AGG  AGG  ACC  TTG  ATG       117
Pro  Gln  Thr  His  Ser  Leu  Gly  Ser  Arg  Arg  Thr  Leu  Met
                 30                        35

CTC  CTG  GCA  CAG  ATG  AGG  AAA  ATC  TCT  CTT  TTC  TCC  TGC       156
Leu  Leu  Ala  Gln  Met  Arg  Lys  Ile  Ser  Leu  Phe  Ser  Cys
 40                  45                       50
```

-continued

```
TTG AAG GAC AGA CAT GAC TTT GGA TTT CCC CAG GAG GAG    195
Leu Lys Asp Arg His Asp Phe Gly Phe Pro Gln Glu Glu
        55                  60                      65

TTT GGC AAC CAG TTC CAA AAG GCT GAA ACC ATC CCT GTC    234
Phe Gly Asn Gln Phe Gln Lys Ala Glu Thr Ile Phe Val
                70                  75

CTC CAT GAG ATG ATC CAG CAG ATC TTC AAT CTC TTC AGC    273
Leu His Glu Met Ile Glu Gln Ile Phe Asn Leu Phe Ser
        80                  85                      90

ACA AAG GAC TCA TCT GCT GCT TGG GAT GAG ACC CTC CTA    312
Thr Lys Asp Ser Ser Ala Ala Trp Asp Glu Thr Leu Leu
                95                  100

GAC AAA TTC TAC ACT GAA CTC TAC CAG CAG CTG AAT GAC    351
Asp Lys Phe Tyr Thr Glu Leu Tyr Gln Gln Leu Asn Asp
105                 110                 115

CTG GAA GCC TGT GTG ATA CAG GGG GTG GGG GTG ACA GAG    390
Leu Glu Ala Cys Val Ile Gln Gly Val Gly Val Thr Glu
            120                 125                 130

ACT CCC CTG ATG AAG GAG GAC TCC ATT CTG GCT GTG AGG    429
Thr Pro Leu Met Lys Glu Asp Ser Ile Leu Ala Val Arg
                135                 140

AAA TAC TTC CAA AGA ATC ACT CTC TAT CTG AAA GAG AAG    468
Lys Tyr Phe Gln Arg Ile Thr Leu Tyr Leu Lys Glu Lys
145                 150                 155

AAA TAC AGC CCT TGT GCC TGG GAG GTT GTC AGA GCA GAA    507
Lys Tyr Ser Phe Cys Ala Trp Glu Val Val Arg Ala Glu
            160                 165

ATC ATG AGA TCT TTT TCT TTG TCA ACA AAC TTG CAA GAA    546
Ile Met Arg Ser Phe Ser Leu Ser Thr Asn Leu Gln Glu
170                 175                 180

AGT TTA AGA AGT AAG GAA GGT GGC TCA GGT GGA TCC GGT    585
Ser Leu Arg Ser Lys Glu Gly Gly Ser Gly Gly Ser Gly
            185                 190                 195

GGA GGC GGA AGC GGC GGT GGA GGA TCA GAG TCC AAA TAT    624
Gly Gly Gly Ser Gly Gly Gly Gly Ser Glu Ser Lys Tyr
                200                 205

GGT CCC CCG TGC CCA TCA TGC CCA GCA CCT GAG TTC CTG    663
Gly Pro Pro Cys Pro Ser Cys Pro Ala Pro Glu Phe Leu
210                 215                 220

GGG GGA CCA TCA GTC TTC CTG TTC CCC CCA AAA CCC AAG    702
Gly Gly Pro Ser Val Phe Leu Phe Pro Pro Lys Pro Lys
            225                 230

GAC ACT CTC ATG ATC TCC CGG ACC CCT GAG GTC ACG TGC    741
Asp Thr Leu Met Ile Ser Arg Thr Pro Glu Val Thr Cys
235                 240                 245

GTG GTG GTG GAC GTG AGC CAG GAA GAC CCC GAG GTC CAG    780
Val Val Val Asp Val Ser Gln Glu Asp Pro Glu Val Gln
            250                 255                 260

TTC AAC TGG TAC GTG GAT GGC GTG GAG GTG CAT AAT GCC    819
Phe Asn Trp Tyr Val Asp Gly Val Glu Val His Asn Ala
                265                 270

AAG ACA AAG CCG CGG GAG GAG CAG TTC AAC AGC ACG TAC    858
Lys Thr Lys Pro Arg Glu Glu Gln Phe Asn Ser Thr Tyr
275                 280                 285

CGT GTG GTC AGC GTC CTC ACC GTC CTG CAC CAG GAC TGG    897
Arg Val Val Ser Val Leu Thr Val Leu His Gln Asp Trp
            290                 295

CTG AAC GGC AAG GAG TAC AAG TGC AAG GTC TCC AAC AAA    936
Leu Asn Gly Lys Glu Tyr Lys Cys Lys Val Ser Asn Lys
300                 305                 310
```

| | | | | | | | | | | | | | |
|---|---|---|---|---|---|---|---|---|---|---|---|---|---|
| GGC | CTC | CCG | TCC | TCC | ATC | GAG | AAA | ACC | ATC | TCC | AAA | GCC | 975 |
| Gly | Leu | Pro | Ser | Ser | Ile | Glu | Lys | Thr | Ile | Ser | Lys | Ala | |
| | | 315 | | | | | 320 | | | | | 325 | |
| AAA | GGG | CAG | CCC | CGA | GAG | CCA | CAG | GTG | TAC | ACC | CTG | CCC | 1014 |
| Lys | Gly | Gln | Pro | Arg | Glu | Pro | Gln | Val | Tyr | Thr | Leu | Pro | |
| | | | | 330 | | | | | 335 | | | | |
| CCA | TCC | CAG | GAG | GAG | ATG | ACC | AAG | AAC | CAG | GTC | AGC | CTG | 1053 |
| Pro | Ser | Gln | Glu | Glu | Met | Thr | Lys | Asn | Gln | Val | Ser | Leu | |
| | 340 | | | | | 345 | | | | | 350 | | |
| ACC | TGC | CTG | GTC | AAA | GGC | TTC | TAC | CCC | AGC | GAC | ATC | GCC | 1092 |
| Thr | Cys | Leu | Val | Lys | Gly | Phe | Tyr | Pro | Ser | Asp | Ile | Ala | |
| | | | 355 | | | | | 360 | | | | | |
| GTG | GAG | TGG | GAG | AGC | AAT | GGG | CAG | CCG | GAG | AAC | AAC | TAC | 1131 |
| Val | Glu | Trp | Glu | Ser | Asn | Gly | Gln | Pro | Glu | Asn | Asn | Tyr | |
| 365 | | | | | 370 | | | | | 375 | | | |
| AAG | ACC | ACG | CCT | CCC | GTG | CTG | GAC | TCC | GAC | GGC | TCC | TTC | 1170 |
| Lys | Thr | Thr | Pro | Pro | Val | Leu | Asp | Ser | Asp | Gly | Ser | Phe | |
| | | 380 | | | | | 385 | | | | | 390 | |
| TTC | CTC | TAC | AGC | AGG | CTA | ACC | GTG | GAC | AAG | AGC | AGG | TGG | 1209 |
| Phe | Leu | Tyr | Ser | Arg | Leu | Thr | Val | Asp | Lys | Ser | Arg | Trp | |
| | | | | 395 | | | | | 400 | | | | |
| CAG | GAG | GGG | AAT | GTC | TTC | TCA | TGC | TCC | GTG | ATG | CAT | GAG | 1248 |
| Gln | Glu | Gly | Asn | Val | Phe | Ser | Cys | Ser | Val | Met | His | Glu | |
| | 405 | | | | | 410 | | | | | 415 | | |
| GCT | CTG | CAC | AAC | CAC | TAC | ACA | CAG | AAG | AGC | CTC | TCC | CTG | 1287 |
| Ala | Leu | His | Asn | His | Tyr | Thr | Gln | Lys | Ser | Leu | Ser | Leu | |
| | | | 420 | | | | | 425 | | | | | |
| TCT | CTG | GGT | AAA | TAG | 1302 | | | | | | | | |
| Ser | Leu | Gly | Lys | | | | | | | | | | |
| 430 | | | | | | | | | | | | | |

HYBRID WITH INTERFERON-ALPHA AND AN IMMUNOGLOBULIN FC LINKED THROUGH A NON-IMMUNOGENIC PEPTIDE

RELATED APPLICATIONS

This application is a continuation-in-part of U.S. application Ser. No. 08/579,211, filed on Dec. 28, 1995, now abandoned.

BACKGROUND OF THE INVENTION

Interferon-α ("IFNα") was among the first of the cytokines to be produced by recombinant DNA technology and has been shown to have therapeutic value in conditions such as inflammatory, viral, and malignant diseases. Several IFNα preparations, including those purified from the natural sources and those generated by recombinant DNA technology, have been used or are being tested in a variety of malignant and viral diseases. IFNα can cause regression of some established tumors and induce positive responses in some viral infections. So far, IFNα has been approved or tested in many countries for indications such as: Kaposi's sarcoma; hairy cell leukemia; malignant melanoma; basal cell carcinoma; multiple myeloma; renal cell carcinoma, hepatitis B; hepatitis C; venereal warts, Herpes I/II, varicella/herpes zoster; and mycosis fungoides.

Most cytokines, including IFNα, have relatively short circulation half-lives since they are produced in vivo to act locally and transiently. The serum half-life of IFNα is only about two to eight hours (Roche Labs. Referon A, Schering Intron A, *Physicians' Desk Reference*, 47th edition, 1993, pp. 2006–2008, 2194–2201). To use IFNα as an effective systemic therapeutic, one needs relatively large doses and frequent administrations. For example, one of the recommended therapeutic strategies for the AIDS-related Kaposi's sarcoma starts with an induction dose of 36 million IU daily for 10 to 12 weeks, administered as an intramuscular or subcutaneous injection, followed by a maintenance dose of 36 million IU, three times a week. (Roche Labs. Referon A, *Physicians' Desk Reference*, 47th edition, 1993, pp. 2006–2008). Such frequent parenteral administrations are inconvenient and painful. Further, toxic effects, which are probably caused by the high dosage, are a problem for certain patients. Skin, neurologic, endocrine, and immune toxicity have been reported. To overcome these disadvantages, one can modify the molecule to increase its circulation half-life or change the drug's formulation to extend its release time. The dosage and administration frequency can then be reduced while increasing the efficacy. It was reported that doses of less than nine million units had been well tolerated, while doses more than 36 million units can induce severe toxicity and significantly alter patient status. (Quesada, J. R. et al., *J. Clin. Oncol.*, 4:234–43, 1986). It is possible to decrease substantially the toxic effects by producing a new form IFNα which is more stable in the circulation and requires smaller doses. Efforts have been made to create a recombinant IFNα-gelatin conjugate with an extended retention time (Tabata, Y. et al., *Cancer Res.* 51:5532–8, 1991). A lipid-based encapsulated IFNα formulation has also been tested in animals and achieved an extended release of the protein in the peritoneum (Bonetti, A. and Kim, S. *Cancer Chemother Pharmacol.* 33:258–261, 1993).

Immunoglobulins of IgG and IgM class are among the most abundant proteins in the human blood. They circulate with half-lives ranging from several days to 21 days. IgG has been found to increase the half-lives of several ligand binding proteins (receptors) when used to form recombinant hybrids, including the soluble CD4 molecule, LHR, and IFN-γ receptor (Mordenti J. et al., *Nature*, 337:525–31, 1989; Capon, D. J. and Lasky, L. A., U.S. Pat. No. 5,116, 964; Kurschner, C. et al., *J. Immunol.* 149:4096–4100, 1992). However, such hybrids can present problems in that the peptide at the C-terminal of the active moeity and the peptide at the N-terminal of the Fc portion at the fusion point creates a new peptide sequence, which is a neoantigen, and which can be immunogenic. The invention relates to a IFNα-Fc hybrid which is designed to overcome this problem and extend the half-life of the IFNα.

SUMMARY OF THE INVENTION

The present invention relates to a hybrid recombinant protein which consists of two subunits. Each subunit includes a human interferon, preferably IFNα, joined by a peptide linker which is primarily composed of a T cell inert sequence, linked to a human immunoglobulin Fc fragment, preferably the γ4 chain. The γ4 chain is preferred over the γ1 chain because the former has little or no complement activating ability.

The C-terminal end of the IFNα is linked to the N-terminal end of the Fc fragment. An additional IFNα (or other cytokine) can attach to the N-terminal end of any other unbound Fc chains in the Fc fragment, resulting in a homodimer for the γ4 chain. If the Fc fragment selected is another chain, such as the μ chain, then, because the Fc fragments form pentamers with ten possible binding sites, this results in a molecule with interferon or other cytokine linked at each of ten binding sites.

The two moieties of the hybrid are linked through a T cell immunologically inert peptide (e.g., Gly Gly Ser Gly Gly Ser Gly Gly Gly Gly Ser Gly Gly Gly Gly Ser (SEQ ID NO:1)). This peptide itself is immunologically inactive. The insertion of this peptide at the fusion point eliminates the neoantigenicity created by the joining of the two peptide moieties. The linker peptide also increases the flexibility of these moieties and allows retention of the biological activity. This relatively long linker peptide helps overcome the possible steric hindrance from the Fc portion of the hybrid, which could interfere with the activity of the hybrid.

The hybrid has a much longer half-life than the native IFNα. Due to the linker, it is also designed to reduce the possibility of generating a new immunogenic epitope (a neoantigen) at what would otherwise be the fusion point of the IFNα and the immunoglobulin Fc segment.

Cytokines are generally small proteins with relatively short half-lives which dissipate rapidly among various tissues, including at undesired sites. It is believed that small quantities of some cytokines can cross the blood-brain barrier and enter the central nervous system, thereby causing severe neurological toxicity. The IFNα linked to Fcγ of the present invention would be especially suitable for treating hepatitis B or C, because these products will have a long retention time in the vasculature (upon intravenous adminstration) and will not penetrate undesired sites.

The specific hybrid described can also serve as a model for the design and construction of other cytokine-Fc hybrids. The same or a similar linker could be used in order to reduce the possibility of generating a new immunogenic epitope while allowing retention of the biological activity. Cytokine-Fc hybrids in which interleukin-2 is the cytokine, or hybrids including other cytokines, could be made using the same techniques.

DETAILED DESCRIPTION OF MAKING AND USING THE INVENTION

The hybrid molecule of the invention includes an interferon moiety linked through a unique linker to an immunoglobulin Fc moiety. Preferably, the C-terminal ends of two interferon moieties are separately attached to each of the two N-terminal ends of a heavy chain γ4 Fc fragment, resulting in a homodimer structure. A unique linker peptide, Gly Gly Ser Gly Gly Ser Gly Gly Gly Gly Ser Gly Gly Gly Gly Ser (SEQ ID NO:1), was created to link the two moieties. The complete nucleotide sequence of the preferred γ4 hybrid (including the linker and the Fc moiety) appears in SEQ ID NO: 7. The linker is located at amino acid residue numbers 189 to 204.

The advantage of the hybrid over the native cytokine is that the half-life in vivo is much longer. The hybrid including interferon and the γ4 chain Fc homodimer is larger than the native interferon. Because the pores in the blood vessels of the liver are large, this larger molecule is more suitable for use in treating hepatitis, where the virus responsible primarily affects the liver.

The linker peptide is designed to increase the flexibility of the two moieties and thus maintain their biological activity. Although the interferon and the immunoglobulin are both of human origin, there is always a possibility of generating a new immunogenic epitope at the fusion point of the two molecules. Therefore, the other advantage of the linker of the invention, which consists mainly of a T cell inert sequence, is to reduce immunogenicity at the fusion point. Referring to SEQ ID NO:7, it can be seen that if the linker (residue numbers 189-204) was not present, a new sequence consisting of the residues immediately before number 189 and immediately after 204 would be created. This new sequence would be a neoantigen for the human body.

Human IFNα is derived from a family of several different genes. More than 24 species have been identified so far, from gene and protein sequence data. They differ from each other by anywhere from a few to a maximum of 35 amino acids. Most of the species have a signal peptide sequence of 23 amino acid residues and a mature amino acid sequence of 166 amino acid residues (Goeddel, D. V. et al., *Nature*, 290:20–26, 1981; Weissmann, C. and Weber, H., *Prog. Nuc. Acid Res. Mol. Biol.* 33:251–300, 1986; Zoon, K. C., *Interferon*, 9:1–12, 1987).

IFNα2 (also called IFNαA) is one of the most intensively studied interferon species. The recombinant version of IFNα2 has been used as a therapeutic for several years. Two IFNα2 recombinant products, IFNα2a and IFNα2b, are now commercially available. They differ only in one amino acid at position 23, and there is no significant difference in biological activity between them (von Gabain, A., et al., *Eur. J. Biochem.* 190:257–61, 1990).

IFNα2a was selected as the fusion partner for the interferon hybrid of the invention, although the IFNα2b or any other interferon species (including IFNβ) can be used as well. It is also possible to make similar constructs with other cytokines, such as interleukin-1 or interleukin-2. The same linker could be used, or another one which is not immunogenic and which maintains the biological activity of the contruct could be substituted.

The advantages of the γ4 chain as the Fc moiety in the hybrid is that it is stable in the human circulation. The γ4 chain (unlike the γ1 chain) also avoids the wide spectrum of secondary biological properties, such as complement fixation and antibody-dependant cell-mediated cytotoxicity (ADCC), which may be undesirable properties.

The cDNA of the IFNα2a can be obtained by reverse transcription and PCR, using RNA extracted from leukocytes which express IFNα. One such cell line, KG-1, can be obtained from the American Type Culture Collection (ATCC) in Rockville, Md., where it is held under number CCL 246. In the procedure used in making the hybrid of the invention, before the RNA extraction, the cells were challenged by Sendai virus to increase their transcription of interferons (Cantell, K. et al., *Methods in Enzymology*, 78A:29–38, Adacemic Press, 1981).

As mentioned above, IFNα is a collection of IFN species and each cell expresses several different IFNα subspecies at the same time. The DNA sequence homology among these species is so high that RT-PCR would probably amplify a group of them instead a specific one. To obtain specifically the IFNα2a cDNA, the PCR primers were designed so that the last nucleotides of the two primers ended at positions where the amino acids coded are unique for IFNα2a. These are position S22 and 161, respectively (See Zoon, K. C. *Interferon*, 9:1–12, 1987).

By using an overlapping PCR technique (Daugherty, B. L. et al., *Nucleic Acids Res.* 19:2471–6, 1991), one can easily ligate two gene segments at any site as desired. However, one drawback of PCR amplification is the relatively high mutation rate (Saiki, R. K. et al., *Science*, 239:487, 1988). Thus, DNA sequencing was also done to check every DNA segment obtained through PCR for lack of mutation. Sequencing can be tedious and time consuming when the size of the segment is over 1 kb, as is the full length IFNα-Fc cDNA. However, a restriction endonuclease site, BamH I, can be incorporated into the linker nucleotide sequence without changing its amino acid sequence. This site is located between the nucleotide numbers 15 and 16 in SEQ ID NO:1.

The two gene segments from PCR can be separately cloned into cloning vectors. This makes the DNA sequencing easier and quicker since both segments are only a few hundred base pairs in length. Once the clones with the correct DNA sequences are identified, the two gene segments can be linked together through the BamH I site. No second round overlapping PCR and subsequent DNA sequencing of the full length segment are required.

There are several ways to express the recombinant protein in vitro, including in *E. coli*, baculovirus, yeast, mammalian cells or other expression systems. The prokaryotic system, *E. coli*, is not able to do post-translational modification, such as glycosylation. But this is probably not a serious problem for the IFNα-Fc hybrid since the native IFNα and immunoglobulin γ4 molecule are not heavily glycosylated. Further, it has been reported that recombinant IFNα without any glycosylation retained its biological activity (Baron, E. and Narula, S., *Bio/technology*, 10:179–190, 1990).

However, the purification of recombinant protein from the *E. coli* lysate can be difficult. The foreign proteins expressed by *E. coli* often aggregate and form insoluble inclusion bodies. Thus, solubilization and subsequent refolding of the inclusion bodies is usually required (Schein, C. H. and Noteborn, H. M., *Bio/technology*, 6:291–294, 1988; Wilkinson, D. L. and Harrison, R. G., *Bio/technology*, 9:443–448, 1991).

The yeast expression system Pichia Pastoris (Invitrogen, San Diego, Calif.) overcomes some of the problems encountered when using the bacterial system. It usually gives a high yield and has the ability to do various post-translational modifications. The expressed foreign protein can be secreted into the culture supernatant where not many other proteins reside, making protein purification and process scale-up much easier. This system was tried first to express either the IFNα-Fc hybrid or the wild type IFNα2a. Unfortunately the IFNα-Fc secreted was found to be partially degraded on SDS-PAGE, whereas the IFNα2a alone was not. The degradation was believed to be caused by the protease activities present in the yeast expression system, as reported by Scorer, C. A. et al., *Gene*, 136:111–9, 1993. The relatively weak spot in the hinge region is the possible target for the proteases.

A mammalian cell expression system for the IFNα-Fc hybrid was also tried. The mammalian expression vector, pCDNA3 (Invitrogen, San Diego, Calif.) which contains a CMV promoter and a NEO resistance gene, was employed. The host cells, NSO cells, were transfected by the pCDNA3/IFNα-Fc expression vector using the electroporation method. The cells were selected by G418 at a concentration of 0.8 mg/ml. The IFNα-Fc expressing clones were identified by ELISA. The hybrid was successfully expressed in this system and there was no degradation.

There are several advantages to this mammalian expression system. First, the recombinant protein is secreted into the culture supernatant and there is no aggregation, thereby simplifying purification. One chromatography step using a protein A column yields a purified IFNα-Fc protein. Also, the protein produced in this system has a glycosylation pattern very similar to the natural molecules since it is expressed by mammalian cells. Further, a native IFNα2a signal peptide sequence is included in the expression vector. Therefore the protein secreted from the cells has an authentic N-terminal, whereas in the *E. coli* or yeast expression systems there either is no signal peptide or a non-IFNα signal peptide is used. Either way, it will bring in additional artificial amino acid residue(s) at the N-terminal end of the recombinant IFNα-Fc.

As mentioned above, the purification of the IFNα-Fc recombinant protein from the culture supernatant is relatively straightforward. The protein with a purity of more than 90%, as judged by SDS-PAGE, can be easily obtained by one step of affinity chromatography with a protein A column.

There are several assay methods available for the measuring of the IFNα bioactivity. Using an antiviral assay, it was demonstrated that the hybrid of SEQ ID NO:7 had a specific activity about 5 to 10 fold higher than a related IFNα-Fc hybrid, in which the linker molecule had the sequence Gly Gly Ser Gly Gly Ser (SEQ ID NO:2), and the Fc portion of the hybrid was derived from human IgG1 rather than IgG4. Nevertheless, although the biologicial activity of the hybrid shown in SEQ ID NO:7 was improved substantially, it was still lower than that of the native IFNα. However, it is expected that this hybrid will have a longer half-life in vivo. This expectation is based on results demonstrating that the related IFNα hybrid with the linker sequence shown in SEQ ID NO:2 and an IgG1 Fc portion showed a much longer half-life, in a mouse model, than did the native IFNα. These pharmacokinetic studies on the related hybrid are summarized in parent application Ser. No. 08/579,211.

Because the hybrid of SEQ ID NO:7 is expected to have a longer half-life in vivo than native IFNα, even though its specific activity is lower, this novel hybrid is expected to be preferred to the native IFNα for clinical use. This is because, as a result of the longer half-life, the Cxt (the area under the concentration vs. time curve) would be up to several hundred times greater than for the native IFNα. This means that at the equivalent molar dosage of the native IFNα and the hybrid, the latter would provide a several hundred fold increased exposure to IFNα, resulting in vastly increased efficacy at the same dosage, and less frequent administration.

In measuring specific activity, molar dosage is preferred instead of expressing activity as units per mass of protein. This is because interferons function through the binding to their specific receptors, which is directly related to the number of molecules present. Also, the molecular weight of the IFNα-Fcγ4, 110 Kd, is more than five-fold larger than that of the wild type IFNα2a, which is 20 kd. Taking this into consideration, measuring activity in units/μmol instead of the units/mg provides a better comparison of activity specifity.

Example 1: Cloning human IFNα cDNA and constructing the IFNα-Fc expression vector $6 \times 10^6$ KG-1 cells (ATCC 246) were incubated with 200 units of Sendai virus at 37° C. overnight. The cells were harvested and washed with PBS throughly. The total RNA was extracted by using the RNA-ZOL RNA isolation kit (BIOTEX, Houston, Tex.) following the procedure provided by the manufacturer. The first-strand cDNA was synthesized by reverse transcription using AMV reverse transcriptase with oligo(dT) as 3' primer in 50 mM Tris-HCl (pH 8.3), 60 mMKCl, and 6 mM $MgCl_2$, incubated at 42° C. for 1 hour. The reaction mixture was used directly as the template for PCR to amplify IFNα cDNA. The 5' primer for PCR contained a Hind III site and the coding sequence for the first 21 amino acids from the IFNα2a leader peptide (SEQ ID NO:3). The 3' primer contained the sequence coding for part of the linker (SEQ ID NO:1) and the last five amino acids of the IFNα2a, and a BamH I site integrated in the linker sequence (SEQ ID NO:4). The PCR buffer contained 50 mM KCl, 10 mMTris-Hcl (pH8.3), 1.5 mM $MgCl_2$, 0.01% gelatin, 0.1 mmol each of dNTP, 0.5 μmol of each primers, 5 μl RT reaction mixture, and 1 unit of Taq DNA polymerase in a total of 50 μl volume. The PCR condition was 94° C. (1 min), 55° C. (2 min), and 72° C. (2 min) for 40 cycles on a GeneAmp PCR System 9600 (Perkin Elmer, Norwalk, Conn.).

The cDNA of the human immunoglobulin γ4 Fc was obtained by reverse transcription and PCR performed the same way as described above. The RNA was extracted from the human tonsil B cells. The 5' primer had the sequence shown in SEQ ID NO:5. The 3' primer had the sequence shown in SEQ ID NO: 6.

The two PCR amplified DNA segments were cloned into pUC18 vectors at sites Hind III/BamH I or sites BamH I/EcoR I respectively. After their DNA sequences were confirmed by DNA sequencing using the kit from USB (Cleveland, Ohio), the two segments were ligated together through the BamH I site by a second round cloning. The full length IFNα-Fc cDNA was then inserted into a mammalian expression vector pCDNA3 (Invitrogen, San Diego, Calif.) through the Hind III and EcoR I sites.

Example 2: Expressing IFNα-Fc in mammalian cells $10^7$ NSO cells were mixed with 10 μg linearized pCDNA3/IFNα-Fc plasmid in 0.8 ml PBS and kept on ice for 5 min. Electroporation was performed at 200 v, 960 μF using Gene Pulser (BioRad, Hircules, Calif.). The cells were then put back on ice for 20 minutes and transferred to a 100 mm tissue culture plate in 10 ml DMEM supplied with 2% FCS. After incubation at 37° C. for two days, the cells were washed and resuspended in the same medium. 0.6 mg/ml G418 was added to start the selection. The cells were plated out in eight 96-well micro plates and incubated at 37° C.

Colonies appeared in one week and they were ready for screening in two weeks. The supernatants from each well with a single colony growing were collected. The IFNα-Fc in the supernatant was quantitatively determined by an ELISA assay employing goat anti-human IgG and anti-human Fc conjugated with horseradish peroxidase. The clones with higher ELISA readings and smaller colony size were selected for subcloning. These colonies were transferred to a 24-well plate and supplied with a medium containing G418. The clone with the highest secretion level was expanded and adapted to grow in a spinner. For large scale preparation, the culture supernatant was collected and passed through a protein A agarose column equilibrized by PBS. The protein bound to the protein A was eluted by 50 mM citric acid (pH 3.0) and concentrated by lyophilization.

Example 3: Characterization of the IFNα-Fc hybrid.

The purity of the recombinant protein isolated from NSO culture medium was examined by SDS-PAGE and Western blot. Only one protein band was visible on the blotted membrane stained by ponceau s for total proteins, showing a homogeneity of the protein preparation. The apparent molecular weight of this protein is about 55 kd under reducing conditions and 110 kd under non-reducing conditions, which is exactly the predicted size for the IFNα-Fc hybrid. The doubling of its apparent molecular weight under non-reducing conditions suggests that the hybrid is in a dimeric form. The recombinant protein can be recognized by both anti-Fc and anti-IFNα antibodies, confirming that it consists of two moieties, the IFNα and the Fc fragment.

The bioactivity assay for the IFNα-Fc was an antiviral assay. Specifically, the assay method used was a modification of the protocol described by Robert M. Friedman et al (Measurement of antiviral activity induced by interferons α, β, and γ, Current Protocols in Immunology, 1994, pp. 6.9.1–6.9.8). Briefly, human lung carcinoma cells (A549, ATCC#CCL 185) were seeded in 96-well plates at a density of 40,000 cells/well and incubated at 37° C. for 24 hours. 1:2 serial diluted IFNα-Fc hybrid or native IFNα (NIH# Gxa01-901-535) were added and incubated at 37° C. for 24 hours. Every sample was done in triplicate. The culture medium was replaced with a fresh one containing encephalomyocarditis virus (ATCC #VR 129B) at a concentration of about 0.1 MOI/cell and incubated at 37° C. for a further 48 hours. The dead cells were washed away by pipetting up and down vigorously with PBS. The attached cells were fixed by 2% formaldehyde and stained by giemsa stain. The plates were rinsed with tap water and allowed to dry. The stained cells were dissolved by methanol and the samples were read spectrophotometrically at 595 nm. The antiviral activity of IFNα-Fc hybrid was calculated by comparing it with the IFNα standard, and was found to be about 30 to 60% of the activity of the IFNα standard.

It should be understood that the terms and expressions used herein are exemplary only and not limiting, and that the scope of the invention is defined only in the claims which follow, and includes all equivalents of the subject matter of those claims.

What is claimed is:

1. A hybrid molecule comprising an interferon molecule joined at its C-terminal end through a peptide linker to the N-terminal end of a first gamma immunoglobulin Fc fragment, the peptide linker having the sequence Gly Gly Ser Gly Gly Ser Gly Gly Gly Gly Ser Gly Gly Gly Gly Ser (the peptide of SEQ ID NO:1), the hybrid molecule having a specific activity of at least $1.1 \times 10^9$ IU/μmole as measured by a virus cytopathic effect inhibition assay.

2. The hybrid molecule of claim 1 in which another interferon molecule is joined at its C-terminal end through another peptide linker having the same sequence to the N-terminal end of the other gamma chain of the immunoglobulin Fc fragment, thereby forming a homodimer.

3. The hybrid molecule of claim 2 in which the interferon molecule is IFNα2a or IFNα2b.

4. The hybrid molecule of claim 2 in which the Fc fragment is a γ4 chain Fc fragment.

* * * * *